(12) United States Patent
Schleck et al.

(10) Patent No.: US 6,472,380 B1
(45) Date of Patent: *Oct. 29, 2002

(54) GLUCOSAMINE SULFATE CALCIUM CHLORIDE COMPOSITION AND PROCESSES FOR THE PREPARATION OF GLUCOSAMINE SULFATE METAL CHLORIDES

(75) Inventors: James R. Schleck, Somerset, NJ (US); Christopher M. Burger, Highstown, NJ (US); Vilas M. Chopdekar, Edison, NJ (US)

(73) Assignee: Jame Fine Chemicals, Inc., Bound Brook, NJ (US)

( * ) Notice: Subject to any disclaimer, the term of this patent is extended or adjusted under 35 U.S.C. 154(b) by 147 days.

This patent is subject to a terminal disclaimer.

(21) Appl. No.: 09/708,197

(22) Filed: Nov. 8, 2000

Related U.S. Application Data

(60) Provisional application No. 60/167,348, filed on Nov. 24, 1999.

(51) Int. Cl.[7] .................. A61K 31/70; C07H 17/02; C07H 17/00; C07H 5/04; C07H 5/06
(52) U.S. Cl. .................. 514/62; 536/17.2; 536/18.7; 536/55.2; 536/55.3
(58) Field of Search .................. 514/62; 536/18.7, 536/55.2, 55.3, 17.2

(56) References Cited

U.S. PATENT DOCUMENTS

| | | | |
|---|---|---|---|
| 3,683,076 A | 8/1972 | Rovati | 424/180 |
| 4,642,340 A | 2/1987 | Senin et al. | 536/55.2 |
| 5,587,363 A | 12/1996 | Henderson | 514/54 |
| 5,599,846 A | 2/1997 | Chopdekar et al. | 514/653 |
| 5,663,415 A | 9/1997 | Chopdekar et al. | 560/68 |
| 5,843,923 A | 12/1998 | Schleck et al. | 514/62 |
| 5,902,801 A | 5/1999 | Schleck et al. | 514/62 |

FOREIGN PATENT DOCUMENTS

| | | | |
|---|---|---|---|
| EP | 0 214 642 A2 | 3/1987 | C07H/5/06 |

*Primary Examiner*—James O. Wilson
*Assistant Examiner*—Everett White
(74) *Attorney, Agent, or Firm*—Jack Matalon

(57) ABSTRACT

Glucosamine compositions comprising the compounds glucosamine sulfate metal chloride, wherein the metal, i.e., the cation is potassium, sodium, magnesium, lithium, calcium, zinc or manganese. The compounds have purity levels of at least about 97%, with water present in a maximum amount of about 10 wt. %, based on the weight of the composition. The compounds are prepared by contacting glucosamine hydrochloride with a hydroxide of the metal in the presence of water to form a first aqueous solution of the free glucosamine base and a chloride of the metal, acidifying the first aqueous solution with sulfuric acid to form a second aqueous solution of glucosamine sulfate and the chloride of the metal, and thereafter freeze-drying the second aqueous solution at a temperature and at a reduced pressure for such period of time that at least about 90 wt. % of the water is removed and decomposition of the compound glucosamine sulfate metal chloride is limited to a maximum of about 3%.

20 Claims, No Drawings

GLUCOSAMINE SULFATE CALCIUM CHLORIDE COMPOSITION AND PROCESSES FOR THE PREPARATION OF GLUCOSAMINE SULFATE METAL CHLORIDES

CROSS-REFERENCE TO RELATED APPLICATIONS

This application claims the benefit of provisional application Ser. No. 60/167,348 filed Nov. 24, 1999.

FIELD OF INVENTION

The invention relates to a glucosamine sulfate calcium chloride composition and to processes for preparing glucosamine sulfate metal chloride compositions. The glucosamine sulfate metal chloride compositions of the invention are true compounds having a purity level of at least about 97%.

BACKGROUND OF THE INVENTION

Glucosamine is a well known and widely used substance for the treatment of rheumatic fever, arthritic and arthosic complaints, in the acute as well as chronic forms, as well as in the treatment of pathological conditions originating from metabolic disorders of the osteo-articular tissue. Although products in the marketplace are labeled as, or referred to as, "glucosamine sulfate" or "stabilized glucosamine sulfate," they are misnomers, since such products are not true compounds, but rather are unreacted mixtures of glucosamine hydrochloride and a salt such as potassium or sodium sulfate.

Mixed salts of glucosamine hydrochloride and alkaline or earth alkaline metal sulfates such as potassium sulfate, and sodium sulfate are well known. Such mixed salts are used rather than glucosamine sulfate alone since the latter is unstable in view of its highly hygroscopic nature and the facility with which its amino group oxidizes if not completely saltified, see, e.g., U.S. Pat. No. 4,642,340 and U.S. Pat. No. 3,683,076 which discloses a mixture of glucosamine sulfate and glucosamine hydroiodide.

Free glucosamine base may be prepared by the method recited in *Chem. Ber.*, volume 75, page 1274. Such method involves the treatment of glucosamine hydrochloride with an ethanolic solution of a tertiary base such as triethylamine. Triethylamine hydrochloride is filtered off and the free glucosamine is then recovered from the reaction mixture. However, triethylamine is a toxic material even in. small quantities and the yield of the free glucosamine base is quite low.

In EP 0 214 642, free glucosamine base is converted to a mixed salt of glucosamine sulfate and potassium chloride by dissolving the glucosamine base in water, adding a stoichiometric quantity of concentrated sulfuric acid to form a solution of glucosamine sulfate in water and dissolving a stoichiometric amount of potassium chloride in the solution. The mixed salt is precipitated from the solution by addition of a precipitant such as isopropanol, stirring the mixture for about 14 hours to complete the precipitation, cooling the reaction mass to 0°C. and recovering the precipitated salt by filtration. This process results in low yields.

SUMMARY OF THE INVENTION

It has now been found possible to prepare compositions comprising true compounds of glucosamine sulfate metal chlorides, wherein the metal, i.e., the cation, comprises potassium, sodium, magnesium, lithium, calcium, zinc or manganese. The compounds will have a purity level of about 97%, preferably at least 99%. Moreover, the processes of the invention avoid the use of toxic reagents such as triethylamine and also avoids the use of precipitants such as isopropanol, thereby permitting substantially quantitative yields with little or no impurities present other than very minor quantities of water.

DETAILED DESCRIPTION OF THE INVENTION

The invention pertains to a novel glucosamine sulfate calcium chloride composition and to processes for preparing glucosamine sulfate metal chloride compositions wherein the meta I comprises potassium, sodium, magnesium, lithium, calcium, zinc or manganese.

In respect to the processes, the compositions comprise:
(a) glucosamine sulfate metal chloride compounds having a purity level of at least about 97%, wherein the metal is selected from the group consisting of potassium, sodium, magnesium, lithium, calcium, zinc and manganese; and
(b) water, present in a maximum amount of about 10 wt. %, based on the weight of the composition.

Preferably, the compounds will have purity levels of at least 99%. Indeed, the processes of the invention typically result in compounds having purity levels in excess of 99%. The principal impurity will be water which is preferably present in a maximum amount of 5 wt. %, based on the weight of the composition. Typically, the processes of the invention will produce compositions with water contents of not greater than 3 wt. %.

Any water present in the compositions of the invention is not to be regarded as an "impurity" in the classical sense. The compositions of the invention are intended to be ingested and minor adjustments in the dosage to be ingested can be readily made to account for such water.

The processes for preparing the compositions of the invention are straightforward and typically result in quantitative yields. The processes involve the following steps:
(a) contacting glucosamine hydrochloride with a hydroxide of a metal selected from the group consisting of potassium, sodium, magnesium, lithium, calcium, zinc and manganese in the presence of water to form an aqueous solution of glucosamine free base and the chloride of the metal;
(b) acidifying the aqueous solution resulting from step (a) with sulfuric acid to form an aqueous solution of glucosamine sulfate and the chloride of the metal; and
(c) recovering the glucosamine sulfate metal chloride compound by freezedrying the solution from step (b) at a temperature and at a reduced pressure for such period of time that: (i) at least about 90 wt. % of the water is removed and (ii) decomposition of the compound is limited to a maximum of about 3%.

Typically, in step (a), the glucosamine hydrochloride and metal hydroxide are contacted in stoichiometric quantities in the presence of sufficient water to form an aqueous solution of the glucosamine free base and the chloride of the metal in a solids concentration of about 15 to about 40 wt. %, preferably 20 to 30 wt. %, based on the weight of the solids plus water. The contacting of the glucosamine hydrochloride and the hydroxide of the metal takes place over a period of time of about 15 minutes to about 4 hours and at temperatures of about 5 to about 45° C. Higher temperatures are undesirable since exposure to such higher temperatures for prolonged periods of time will lead to decomposition, as evidenced by a yellowing of the solution.

Typically, in step (b), the aqueous solution of the glucosamine free base and the chloride of the metal is contacted with a stoichiometric quantity of sulfuric acid in the presence of sufficient water to form a concentration of solids of about 15 to about 40 wt. %, preferably 20 to 30 wt. %, based on the weight of the solids and water. Since the addition of the sulfuric acid to the aqueous solution results in an exothermic reaction, it is desirable that the sulfuric acid be gradually added, i.e. the contacting in step (b) should occur over a period of time of about 15 minutes to about 2 hours while maintaining a temperature of about 5 to about 45° C. In view of the exothermic reaction which occurs in step (b), the reaction mixture is desirably cooled in an ice bath to maintain the temperature in the foregoing range. Higher temperatures are undesirable since exposure to such higher temperatures for prolonged periods of time will lead to decomposition, as evidenced by a yellowing of the solution.

The freeze-drying in step (c) is typically carried out at a pressure of not greater than about 800 milliTorr, preferably 300 to 500 milliTorr, and at a temperature of about −60 to about 0° C., preferably −40 to −5° C.

The processes of the invention avoid the use of precipitants such as isopropanol, acetone, dioxane, etc. in order to recover the glucosamine sulfate metal chloride from the aqueous reaction mixture.

It has also been found that if removal of the water by distillation is used to recover the glucosamine sulfate metal chloride, some decomposition of the product occurs, even if the distillation is carried out at moderate temperatures of about 50° C. and at a pressure of about 20 mm Hg. Decomposition of the product is evidenced by a yellowing of the product and a shift in taste from sweetish and slightly salty to a bitter taste. When the water is attempted to be removed under vacuum at a pressure of about 20 mm Hg at ambient temperatures, significant foaming of the reaction mass occurs which prevents the water from being distilled off without also causing the product to flow out of the flask containing the aqueous solution.

The following examples serve to illustrate the embodiments of this invention. Unless otherwise indicated to the contrary, all parts and percentages are on a weight basis.

EXAMPLE 1

A one-liter beaker equipped with a magnetic stirrer was charged with 307 g of water. Thereafter, 107.8 g (0.25 m) of glucosamine hydrochloride were added with stirring and the reaction mixture was warmed to 35° C. Subsequently, 19.5 g (0.25 m) of calcium hydroxide were added with agitation. Stirring was continued for 2 hours during which most of the solids went into solution. The solution was filtered to remove a small quantity of precipitate and the pH of the filtrate (430 g) was determined to be 8.6. Thereafter, 49 g (0.25 m) of sulfuric acid diluted with an equal part of water were slowly added over a 15 minute period with stirring while the beaker was in an ice bath and the temperature was maintained at about 15° C. A sample of the resultant reaction mixture (pH=4.0) was then assayed for specific rotation which was measured at 20° C. to be 56°. Water was then stripped off from the resultant solution by freeze drying at a pressure of 200 milliTorr and at a temperature of about −40 to −5° C. The yield of the glucosamine sulfate calcium chloride composition was 135.5 g (95.5%) and the product had a specific rotation of 55.5° measured at 20° C.

EXAMPLE 2

Example 1 was repeated using 300 g of water and 14.6 g (0.25 m) of magnesium hydroxide in place of the calcium hydroxide. Stirring was continued for 2 hours during which most of the solids went into solution. The solution was filtered to remove a small quantity of precipitate and the pH of the filtrate (418 g) was determined to be 8.6. Thereafter, 49 g (0.25 m) of sulfuric acid diluted with an equal part of water were slowly added over a 15 minute period with stirring while the beaker was in an ice bath and the temperature was maintained at about 15° C. A sample of the resultant reaction mixture (pH=4.0) was then assayed for specific rotation which was measured at 20° C. to be 56.5° Water was then stripped off from the resultant solution by freeze drying at a pressure of 200 milliTorr and at a temperature of about −40 to −5° C. The yield of the glucosamine sulfate magnesium chloride composition was 132.5 g (96%) and the product had a specific rotation of 56° measured at 20° C.

EXAMPLE 3

Example 1 was repeated using 291 g of water and 21 g (0.5 m) of lithium hydroxide in place of the calcium hydroxide. Stirring was continued for 2 hours during which most of the solids went into solution. The solution was filtered to remove a small quantity of precipitate and the pH of the filtrate (415 g) was determined to be 8.5. Thereafter, 49 g (0.25 m) of sulfuric acid diluted with an equal part of water were slowly added over a 15 minute period with stirring while the beaker was in an ice bath and the temperature was maintained at 10–12° C. A sample of the resultant reaction mixture (pH=4.3) was then assayed for specific rotation which was measured at 20° C. to be 58°. Water was then stripped off from the resultant solution by freeze drying at a pressure of 200 milliTorr and at a temperature of about −40 to −5° C. The yield of the glucosamine sulfate lithium chloride composition was 131 g (96.8%) and the product had a specific rotation of 57.5° measured at 20° C.

EXAMPLE 4

Example 1 was repeated using 330 g of water and 28.05 g (0.5 m) of potassium hydroxide in place of the calcium hydroxide. Stirring was continued for 2 hours during which most of the solids went into solution. The solution was filtered to remove a small quantity of precipitate and the pH of the filtrate (460 g) was determined to be 9.0. Thereafter, 49 g (0.25 m) of sulfuric acid diluted with an equal part of water were slowly added over a 15 minute period with stirring while the beaker was in an ice bath and the temperature was maintained at about 15° C. A sample of the resultant reaction mixture (pH=4.3) was then assayed for specific rotation which was measured at 20° C. to be 52°. Water was then stripped off from the resultant solution by freeze drying at a pressure of 200 milliTorr and at a temperature of about −40 to −5° potassium chloride composition was 147 g (97%) and the product had a specific rotation of 51.5° measured at 20° C.

EXAMPLE 5

Example 1 was repeated using 310 g of water and 20 g (0.5 m) of sodium hydroxide in place of the calcium hydroxide. Stirring was continued for 2 hours during which most of the solids went into solution. The solution was filtered to remove a small quantity of precipitate and the pH of the filtrate (434 g) was determined to be 9.0. Thereafter, 49 g (0.25 m) of sulfuric acid diluted with an equal part of water were slowly added over a 15 minute period with stirring while the beaker was in an ice bath and the temperature was maintained at about 15° C. A sample of the resultant reaction mixture (pH=4.0) was then assayed for specific rotation which was measured at 20° C. to be 55°. Water was then stripped off from the resultant solution by freeze drying at a pressure of 200 milliTorr and at a temperature of about −40 to −5° C. The yield of the glucosamine sulfate sodium chloride composition was 138 g (96%) and the product had a specific rotation of 55° measured at 20° C.

EXAMPLE 6

Example 1 was repeated using 322 g of water and 25.4 g (0.25 m) of zinc hydroxide in place of the calcium hydroxide. Stirring was continued for 2 hours during which most of the solids went into solution. The solution was filtered to remove a small quantity of precipitate and the pH of the filtrate (446 g) was determined to be 9.0. Thereafter, 49 g (0.25 m) of sulfuric acid diluted with an equal part of water were slowly added over a 15 minute period with stirring while the beaker was in an ice bath and the temperature was maintained at about 15° C. A sample of the resultant reaction mixture (pH=4.0) was then assayed for specific rotation which was measured at 20° C. to be 53°. Water was then stripped off from the resultant solution by freeze drying at a pressure of 200 milliTorr and at a temperature of about −40 to −5° C. The yield of the glucosamine sulfate sodium chloride composition was 138 g (96%) and the product had a specific rotation of 52.5° measured at 20° C.

What is claimed is:

1. A composition comprising:
   (a) the compound glucosamine sulfate calcium chloride, having a purity level of at least about 97%; and
   (b) water, present in a maximum amount of about 10 wt. %, based on the weight of the composition.

2. The composition of claim 1 wherein the purity level is at least 99%.

3. The composition of claim 1 wherein water is present in a maximum amount of 5 wt. %, based on the weight of the composition.

4. The composition of claim 3 wherein the water is present in a maximum amount of 3 wt. %, based on the weight of the composition.

5. A process for preparing a composition comprising the compound glucosamine sulfate metal chloride, wherein the metal is selected from the group consisting of potassium, sodium, magnesium, lithium, calcium, zinc and manganese, said compound having a purity level of at least about 97%, which comprises the steps of:
   (a) contacting glucosamine hydrochloride with a hydroxide of said metal in the presence of water to form an aqueous solution of glucosamine free base and the chloride of said metal;
   (b) acidifying the aqueous solution resulting from step (a) with sulfuric acid to form an aqueous solution of glucosamine sulfate and the chloride of said metal; and
   (c) recovering the compound by freeze-drying the solution from step (b) at a temperature and at a reduced pressure for such period of time that: (i) at least about 90 wt. % of the water is removed and (ii) decomposition of the compound glucosamine sulfate metal chloride is limited to a maximum of about 3%.

6. The process of claim 5 wherein in step (a), the glucosamine hydrochloride is contacted with a stoichiometric quantity of the hydroxide of the metal in the presence of sufficient water to form a solids concentration of about 15 to about 40 wt. %, based on the weight of water plus solids, and the contacting in step (a) takes place over a period of time of about 15 minutes to about 4 hours.

7. The process of claim 6 wherein the water is present in step (a) in an amount such that the solids concentration is in the range of 20 to 30 wt. %, based on the weight of water plus solids.

8. The process of claim 5 wherein in step (b), the aqueous solution of glucosamine free base and the chloride of said-metal are contacted with a stoichiometric quantity of the sulfuric acid in the presence of sufficient water to form a solids concentration of about 15 to 40 wt. %, based on the weight of water plus solids and the contacting in step (b) takes place over a period of about 15 minutes to about 4 hours.

9. The process of claim 8 wherein the water is present in step (b) in an amount such that the solids concentration is in the range of 20 to 30 wt. %, based on the weight of water plus solids.

10. The process of claim 9 wherein the metal comprises manganese.

11. The process of claim 5 wherein step (a) takes place at a temperature in the range of about 5 to about 45° C.

12. The process of claim 5 wherein step (b) takes place at a temperature in the range of about 5 to about 45° C.

13. The process of claim 5 wherein the freeze-drying is carried out at a pressure of not greater than about 800 milliTorr and at a temperature in the range of about −60 to about 0° C.

14. The process of claim 13 wherein the freeze-drying is carried out at a pressure in the range of 300 to 500 milliTorr and a temperature in the range of −40 to −5° C.

15. The process of claim 5 wherein the metal comprises potassium.

16. The process of claim 5 wherein the metal comprises sodium.

17. The process of claim 5 wherein the metal comprises magnesium.

18. The process-of claim 5 wherein the metal comprises lithium.

19. The process of claim 5 wherein the metal comprises calcium.

20. The process of claim 5 wherein the metal comprises zinc.

* * * * *